United States Patent [19]

Stern et al.

[11] Patent Number: 4,900,311

[45] Date of Patent: Feb. 13, 1990

[54] HYPODERMIC SYRINGE

[76] Inventors: Lawrence Stern, 5 Malcolm St., Morristown, N.J. 07960; Thomas Stern, 550 Harold St., Staten Island, N.Y. 10314

[21] Appl. No.: 280,637

[22] Filed: Dec. 6, 1988

[51] Int. Cl.$^4$ .............................................. A61M 5/32
[52] U.S. Cl. .................................... 604/198; 604/263
[58] Field of Search ................ 604/198, 187, 263, 195

[56] References Cited

U.S. PATENT DOCUMENTS 4,664,654  5/1987  Strauss ................................. 604/198
4,795,432  1/1989  Karczmer ......................... 604/198 X
4,813,940  3/1989  Parry ..................................... 604/198

Primary Examiner—John D. Yasko
Attorney, Agent, or Firm—Abelman Frayne Rezac & Schwab

[57] ABSTRACT

A hypodermic syringe has a needle guard of elliptical cross section which is releasable by compressing the needle guard along its major axis, and, which can be moved between an extended and a retracted position when released. Optionally, a compression spring is provided for urging the needle guard towards an extended position.

8 Claims, 3 Drawing Sheets

HYPODERMIC SYRINGE

FIELD OF THE INVENTION

This invention relates to an hypodermic syringe for use in administrating subcutaneous or intravenous injections to persons and animals. While not limited thereto, the invention has particular application for use in hazardous situations in which the patient may possibly or actually be infected with a fatally lethal and incurable virus, microvirus or bacteria.

BACKGROUND OF THE INVENTION

Hypodermic syringes are well-known in the art, including pre-sterilized syringes having a protective cap over the cannula or needle, and which is to be removed immediately prior to administering an injection. The cover is intended subsequently to be replaced over the needle after use of the syringe.

However, at this point, the cannula or needle of the syringe has been contaminated by its use on the patient, and, the needle or cannula itself is potentially lethal, in that it then is a carrier of the virus, microvirus, or bacteria. Careless handling, or, in the absence of the protective cap, can result in the user unintentially being pricked, scratched or cut by the sharpened end of the needle, this resulting in infection of the user.

Numerous proposals have been made to avoid this occurrence, but none has been entirely successful.

During use, sudden retraction of the needle into the syringe by spring force, as has been prior proposed, can cause fracturing of the needle within the patient. It can also cause splattering of contaminants on the needle onto the hands of the user, and possibly into the user's eyes in the event that a visor is not worn by the user. Also, the impact of retraction of the needle under spring force can cause an impact on the syringe, resulting in accidental dropping of the syringe, with possible dangerous consequences.

Other prior proposals involve a manually retractable and manually extendable needle guard. However, such needle guards require the use of both hands for them to be forced manually into the extended position in order to break the holding force of a resiliently engaged retaining member. If the user's hand should slip off the needle guard during the extension of the needle guard, there again is the possibility of the user's hand being impaled by the unprotected needle.

SUMMARY OF THE INVENTION

It is an object of this invention to materially reduce the hazards to the user in using a hypodermic syringe, by providing a syringe assembly having an axially slidable needle guard that is releasable and retractable under manual force, and which is then lockable in a retracted position, and which subsequently can be released and extended under manual force for it to shroud the used needle.

According to the present invention, in order to ready the syringe for use, the user grasps the barrel of the syringe with one hand, and then grasps the needle guard with the other hand, subsequent to which the needle guard is squeezed using a single hand to release a locking projection on the needle guard from a retaining notch in the barrel. The guard can then be slid axially of the barrel of the syringe, with the locking projection travelling within an axial slide track in the barrel.

Having reached the fully retracted position of the needle guard, the locking projection enters a retaining notch at the other end of the axial slide track to lock the needle guard in its retracted position.

In order to permit the release of the locking projection from the retaining notch, the barrel is formed of circular cross section, and the needle guard is formed of elliptical cross section with the locking projection positioned on the minor axis of the ellipse and extending radially inwardly of the bore of the needle guard. Thus, squeezing of the needle guard along its major axis will cause radially outward movement of the locking projection to withdraw it from the retaining notch, permitting the locking projection then to slide within an axial channel formed in the outer surface of the syringe barrel.

When using the syringe, the user's fingers engage holding tabs on the syringe barrel to provide the required axial force on the syringe, this further minimizing the possibility of the user being impaled by the needle. Also, the user's fingers are at that time positioned in engagement with the needle guard and act to retain the locking projection firmly seated within the retaining notch.

Having used the syringe to effect either an injection on the patient, or withdrawal of blood, the user then again squeezes the needle guard on its major axis using a single hand to free it for return movement longitudinally of the barrel of the syringe, the locking projection travelling within the axial slide track to return the locking projection to the first retaining notch.

This forward movement of the needle guard to its extended position can be under the assist of a spring reacting between the needle guard and the barrel of the syringe. If such a spring assist is provided, then, movement of the needle guard to its extended position proceeds under the manual control of the user, in that the needle guard is at that time being grasped by one of the user's hands, which is used to squeeze the needle guard.

Thus, both of the user's hands are located out of proximity to the sharpened end of the cannula or needle, and in a location of maximum safety.

In another preferred embodiment of the invention, the syringe barrel is provided with circumferentially extending slide tracks at the opposite ends of the axial slide track, the circumferentially extending portions of the slide track incorporating either indents or projections providing retaining notches for cooperation with the locking projection formed internally of the needle guard.

In another preferred embodiment of the invention, in which the syringe is supplied with the needle guard retracted, co-operating formations are provided on the syringe barrel and needle that will permit movement of the needle guard to an extended position but which inhibit reverse movement of the needle guard.

Optionally, the needle guard is closed by a removable cap, and is further closed by a frangible diaphragm which is punctured by the needle upon retraction of the needle guard. Puncturing of the diaphragm will provide a clear indication that the syringe has been used.

DESCRIPTION OF THE DRAWINGS

Preferred embodiments of the present invention will now be described with reference to the accompanying drawings, in which.

DESCRIPTION OF THE PREFERRED EMBODIMENTS

Figure 1:
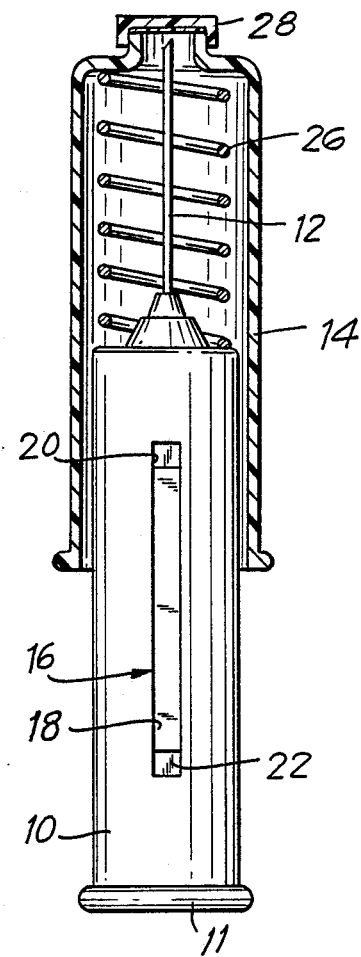
FIG. 1 is a front elevation of the syringe of the present invention, showing the needle guard in cross-section, and in an extended position.

The syringe of the present invention includes, as is conventional, a barrel 10 having finger engageable tabs. A plunger is axially slidable within the barrel, the plunger having been omitted for the purpose of clarity.

Extending axially from the barrel 10 is a hollow needle or cannula 12, which is secured in the end of the barrel 10 in any convenient manner, such as the barrel 10 having been molded in-situ about one end of the needle 12.

Positioned externally of the syringe barrel 10 is a needle guard 14, the needle guard 14 being formed of any suitable resilient and compliant plastics material such as polyvinyl chloride, the needle barrel 10 being formed from andy suitable material, such as a substantially rigid plastics material such as polymethacrylate.

Extending axially of the syringe barrel 10 is a slide track indicated generally at 16, the slide track comprising an axially linear groove 18.

Figure 2:
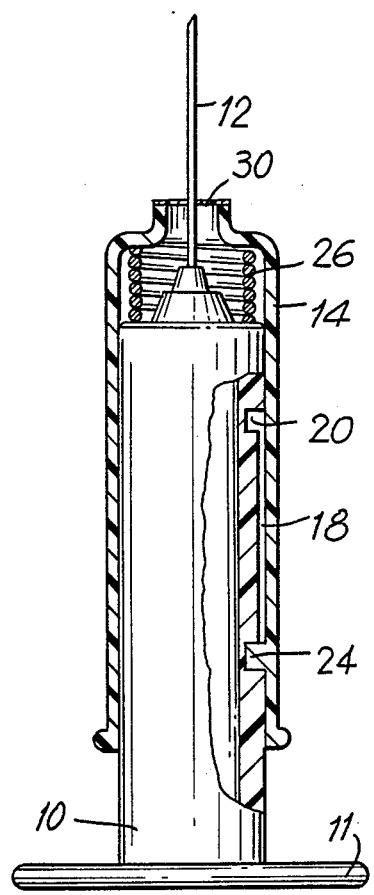
FIG. 2 is a view similar to FIG. 1, but rotated through 90° and showing the needle guard in a retracted position.

Located internally within the needle guard 14 is a radially inwardly extending projection 24 of a shape complimentary to the transverse cross-section of slide track 18, the projection 24 being moveable along the slide track 18 in order to permit retraction of the needle guard 14 from the extended position shown in FIG. 1 to the retracted position shown in FIG. 2. As will be appreciated, the track and the projection could be reversed, the track being provided within the needle guard, and the projection being provided on the needle barrel.

Optionally, a compression spring 26 is positioned internally of the needle guard 12 and reacts against one end of the needle guard and the juxtaposed end of the syringe barrel. The purpose of this spring 26 is to ensure that the needle guard 14 is moved to an extended positioned at all times other than when it is intentionally latched in the retracted position.

Conveniently also, the needle guard is provided with a removable closure cap 28, and, is provided with a frangible diaphragm 30 underlying the cap 28, the diaphragm 30 being puncturable by the needle 12 upon retraction of the needle guard 14.

Figure 3:
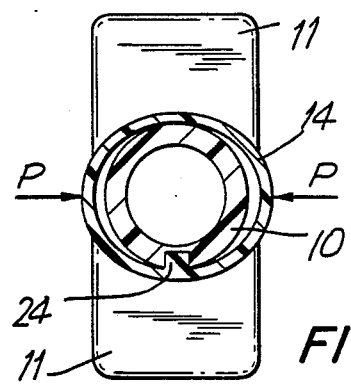
FIG. 3 is a transverse cross-section through the syringe illustrating the cross-section of a needle guard of elliptical cross-section.
Figure 4:
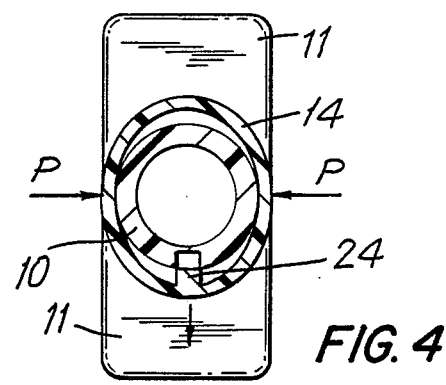
FIG. 4 is a cross-sectional view corresponding with FIG. 3 and showing the needle guard when compressed in the direction of its major axis.

As more clearly illustrated in FIGS. 3 and 4, the needle guard 14 is formed for it to be other than circular. As illustrated in FIG. 3, the needle guard is formed elliptical in transverse cross-section, with the projection 24 lying on the minor axis of the ellipse, and the major axis extending perpendicularly thereto. The projection 24 can be received within one of two retaining notches 20, 22 located at opposite axial ends. of the slide track 18.

In an initial condition, the projection 24 extends radially inwardly into locking engagement with the retaining notch 20, to hold the needle guard immoveable relative to the syringe barrel.

As is illustrated in FIG. 4, the application of manual pressure along the major axis of the needle guard 14 in the direction of the arrows P-P in FIGS. 3 and 4 will cause movement of the projection 24 in a direction radially outwardly of the axis of the syringe barrel 10, and out of engagement within the retaining notch 20 in the needle barrel 10.

The needle guard 14 is at that time freed for movement axially of the syringe barrel 10, this movement being guided by the projection 24 riding within the axially extending groove 18.

Having reached the end of its permissible travel, the projection 24 snaps into and then becomes engaged within the retaining notch 22 at the opposite axial end of the slide track 18, to lock needle guard 14 in the retracted position shown in FIG. 2.

This retraction is effected against the bias of the spring 26, in the event that such a spring is provided. In the event that the user should release the needle guard 14 prior to its being latched in a fully retracted position, or, the user releases the projection 24 by again squeezing the needle guard, then, the needle guard 14 will be returned to its initial position as shown in FIG. 1.

The locking will proceed automatically due to the resilience of the needle guard 14, which inherently will attempt to return to its elliptical formation as illustrated in FIG. 3.

After use of the syringe, the needle guard 14 is unlocked in exactly the same manner as that previously described. This unlocking, requires that the syringe assembly be grasped by at least one of the users hands, and effectively maintains the user's hands isolated from the needle 12, which at that time is possibly contaminated.

Figure 5:
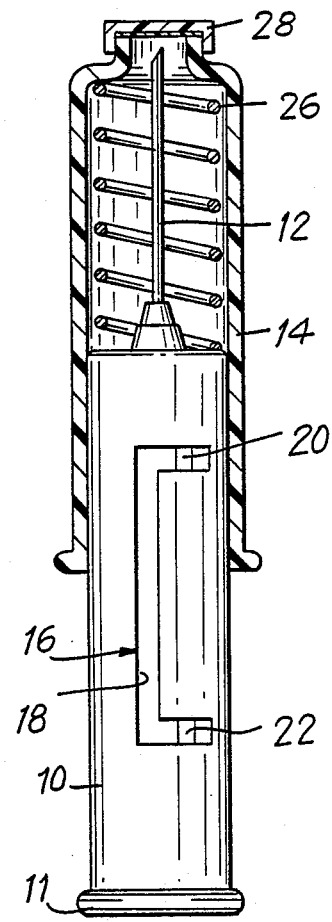
FIGS. 5 and 6 illustrate a modification of FIGS. 1 and 2.
Figure 6:
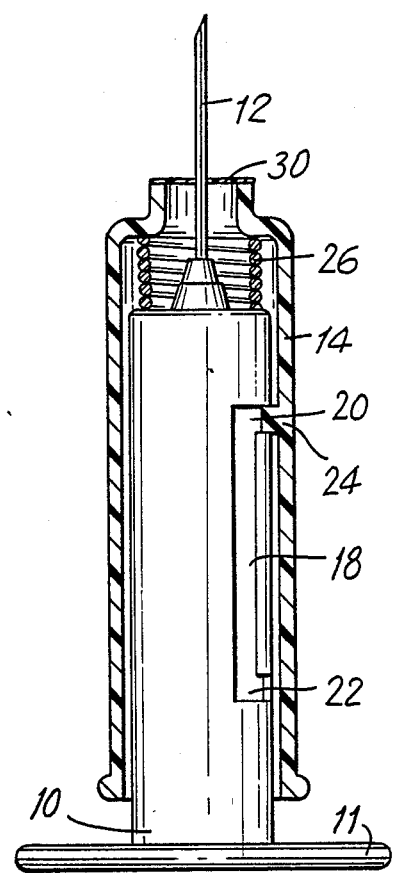

An even more positive lock can be provided by providing circumferential extensions of the slide track 18 at the opposite axial ends thereof, as illustrated in FIGS. 5 and 6, in which the same reference numbers have been used to identify parts in common with FIGS. 1 and 2. In FIGS. 5 and 6, a user is required to use both hands to retract or extend the needle guard, this requiring relative rotational movements of the needle guard and barrel prior to axial relative movement between those members.

As will be appreciated, various modifications in the structure illustrated can be effected without departing from the scope of the invention as defined in the appended claims. For example, if the needle 12 is a short needle, then, the slide track 18 can be arranged as a scroll cam with indentations at its respective opposite ends, such that rotation of the needle guard relative to the barrel 10 after release of the projection 24 from the indentation 20 will automatically cause retraction of the needle guard 14 against the bias of the spring 26, the spring 26 being available to return the needle guard 14 to its extended position at any time prior to locking of the needle guard in its retracted position. Further, as will be readily appreciated, instead of being arranged such that a reverse rotational movement of the needle-barrel is required to lock it, as in FIGS. 5 and 6, the circumferentially extending portions at opposite ends of the slide track 18 could be oppositely extending such that a first turn is required to move the projection 24 into the groove 18, and, second turn in the same direction is required to re-lock the needle guard when in its retracted position, and vice versa.

Figure 7:
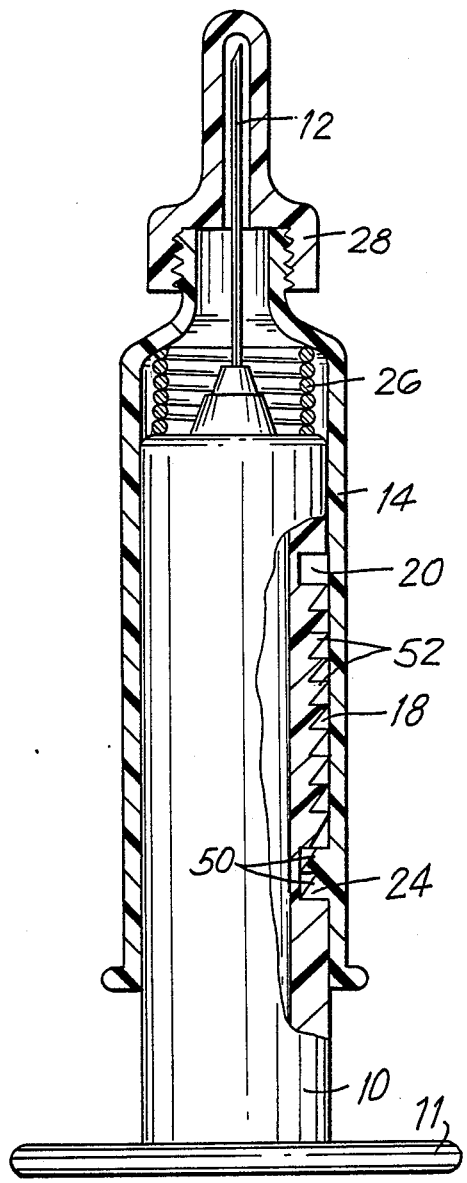
FIG. 7 illustrated a further modification.

The syringe could be supplied with the needle guard in a retracted position and ready for use. After use, the needle guard can then be extended and locked to provide safety to the user, in which event, and as illustrated in FIG. 7, the projection 24 and the bottom wall of the axial groove 18 can be formed as ratchet teeth 50, which will permit movement of the needle guard to an extended position, but, which will inhibit return movement of the needle guard. This can readily be accomplished by making the distance on major axis at the inner face of the needle guard just sufficient to cause release of the projection 24 from the retaining notch 22, subsequent to which the projection 24 can be ratcheted over the rigid teeth 52 of the syringe barrel, this being permitted by the resilience of the material from which the needle guard is formed, and its ability to stretch to a limited extent.

We claim:

1. A hypodermic syringe, including:
 a syringe barrel of circular cross-section having a hypodermic needle attached to an otherwise closed end thereof and extending coaxially of the longitudinal axis of said syringe barrel;
 a retractable and extendable needle guard of elliptical tubular cross-section, said guard being slidably mounted on said syringe barrel for movement axially of said syringe barrel between a retracted position and an extended position;
 locking means provided on one of said syringe barrel and said needle guard, said locking-means including a locking projection on one of said barrel and guard which is received within an axially extending guideway formed in the other of said barrel and guard, said guideway including a retaining notch at each axial end of said guideway, said locking projection being positioned on the minor axis of said elliptical cross-section;
 whereby, compression of said needle guard along its major axis will cause retraction of said locking projection from said retaining notch and permit movement of said needle guard axially of said syringe barrel under the guidance of said locking projection travelling within said guideway, said needle guard being lockable in a selected one of said retracted and extended positions by engagement of said locking projection by the engagement of said locking projection with a selected one of said retaining notches.

2. The hypodermic syringe of claim 1, including a compression spring interposed between said syringe barrel and said needle guard and acting at all times to move said needle guard to an extended position.

3. The hypodermic syringe of claim 1, including an end cap detachably affixed to said needle guard.

4. The hypodermic syringe according to claim 1, including a rupturable diaphragm extending across an open end portion of said needle guard, and which is rupturable by said hypodermic needle upon retraction of said needle guard.

5. The hypodermic syringe of claim 1, in which said guideway includes an axially straight central portion extending axially of said syringe barrel, and an arcuate portion at each end thereof extending circumferentially of said syringe barrel, each arcuate portion incorporating a retaining notch for the reception of said locking projection.

6. The hypodermic syringe of claim 1, in which said syringe barrel is formed from a polymethacrylate material, and said needle guard is formed from a resilient polyvinylchloride material.

7. The hypodermic syringe if claim 1, including cooperating formations on said guideways and projection permitting movement of said needle guard from said retracted position towards said extended position and inhibiting reverse movement thereof.

8. The hypodermic syringe of claim 1, in which a bottom wall of said guideway is formed with ratchet teeth and said locking projection is shaped to cooperate projection providing for movement of said needle guard from a retracted position towards an extended position, and inhibiting reverse movement of said needle guard from said extended position towards said retracted position.

* * * * *